United States Patent
Gao et al.

(10) Patent No.: US 7,123,955 B1
(45) Date of Patent: Oct. 17, 2006

(54) CONTROL METHOD AND SYSTEM AND THE SENSE ORGANS TEST METHOD AND SYSTEM BASED ON ELECTRICAL STEADY STATE INDUCED RESPONSE

(75) Inventors: Xiaorong Gao, Beijing (CN); Shangkai Gao, Beijing (CN); Fusheng Yang, Beijing (CN)

(73) Assignee: Tsinghua University, Beijing (CN)

( * ) Notice: Subject to any disclaimer, the term of this patent is extended or adjusted under 35 U.S.C. 154(b) by 633 days.

(21) Appl. No.: 10/111,801

(22) PCT Filed: Oct. 30, 2000

(86) PCT No.: PCT/CN00/00410

§ 371 (c)(1),
(2), (4) Date: Aug. 12, 2002

(87) PCT Pub. No.: WO01/32078

PCT Pub. Date: May 10, 2001

(30) Foreign Application Priority Data

Oct. 29, 1999 (CN) ................................ 99 1 22161

(51) Int. Cl.
*A61B 5/0476* (2006.01)
*G09B 21/00* (2006.01)
(52) U.S. Cl. ................................. 600/544; 340/825.19
(58) Field of Classification Search ............... 600/544, 600/545; 340/825.19
See application file for complete search history.

(56) References Cited

U.S. PATENT DOCUMENTS

| | | | | |
|---|---|---|---|---|
| 4,244,376 A | * | 1/1981 | Fisher et al. | 600/544 |
| 4,493,539 A | | 1/1985 | Cannon, Jr. | 351/205 |
| 4,651,145 A | | 3/1987 | Sutter | 340/706 |
| 4,676,611 A | * | 6/1987 | Nelson et al. | 600/544 |
| 4,832,480 A | | 5/1989 | Kornacker et al. | 351/246 |
| 4,926,969 A | * | 5/1990 | Wright et al. | 600/544 |
| 5,023,783 A | * | 6/1991 | Cohen et al. | 600/559 |
| 5,331,969 A | | 7/1994 | Silberstein | |
| 5,638,825 A | | 6/1997 | Yamazaki et al. | |

\* cited by examiner

*Primary Examiner*—Eric F. Winakur
(74) *Attorney, Agent, or Firm*—Dykema Gossett PLLC

(57) ABSTRACT

A control method and a sense organ testing method based on steady state brain evoked response include the steps of: generating one or multiple stimulus signal(s) varying in various frequencies that can be sensed by sense organs of human subject; detecting the brain electrical signal of stimulated human subject; analyzing the detected brain electrical signal to extract the characteristic physical quantity corresponding to the frequency of a stimulus signal; and, according to the characteristic physical quantity, controlling a specific device corresponding to the stimulus signal to perform a preprogrammed operation or objectively evaluating the condition of the sense organ of the subject.

65 Claims, 5 Drawing Sheets

CONTROL METHOD AND SYSTEM AND THE SENSE ORGANS TEST METHOD AND SYSTEM BASED ON ELECTRICAL STEADY STATE INDUCED RESPONSE

FIELD OF THE INVENTION

The present invention relates to a method of and a system for controlling devices such as computers based on brain electrical signal, more particularly, relates to a method of and a system for controlling devices such as computers based on steady state brain evoked response, and a method of and a system for objectively testing sense organs based on steady state brain evoked response.

TECHNICAL BACKGROUND

Brain-machine interface is a direct communication and control path established between human brain and computer or other electronic devices. Through this path, one can express himself or operate apparatus directly by his activity of brain without speaking or actions of his limbs.

Different from ordinary man-machine interfaces, a brain-machine interface does not need muscular responses of any type, but merely detects the signal representing responsive or purposeful activity of brain.

A control device based on brain-machine interface may achieve the purpose of controlling a target apparatus without one's speaking or actions of limbs.

Different from subjective sense organ testing systems, an objective sense organ testing system based on brain-machine interface does not need speaking or actions of limbs of the person to be tested for expressing his subjective consciousness, but merely detects the signal representing responsive or purposeful activity of his brain. Thus the system can provide objectivity and justness.

The followings are some existing methods of performing brain electrical signal control.

1. The Method Based on Event Related Brain Electrical Signal

For instance, prior to starting an autonomic motion, there exists so-called event related desynchronized component associated with the motion in one's brain electrical signal, which is substantially an evoked brain electrical signal. We may identify the event related signal in the recorded brain electrical signal, and use the same for performing a certain kind of control.

Pfurtscheller et al. carried out a series of BCI (Brain-Computer Interface) research on the basis of such physiological phenomenon. A subject (testee) faced an object displayed on the right or left of a display, and prepared to press a button with his (or her) left or right forefinger according to the object's position. Then after about one second, there appeared a cross cursor at the center of the display. The subject pressed the button. The brain electrical signals used for classification are those appeared in the activity preparing phase between the appearance of the object and the appearance of the cursor. In this way, a template was obtained through learning, whereby the activity of right hand or left hand could be predicted. ("Brain-computer Interface—A New Communication Device foe Handicapped Persons", J Microcomput Appl, 1993, 16:293–299; "Prediction of the Side of Hand Movements from Single Trial Multichannel EEG Data Using Neural Networks" Electroenceph Clin Neurophsiol, 1992, 82:313–315).

2. The Methods Based on Evoked Electrical Brain Signal

FIG. 1 is a schematic drawing that depicts a prior art system carrying a certain kind of control based on evoked brain electrical signal. The steps of this method comprises: giving a subject some stimulus; recording and identifying the brain electrical signal evoked under various stimuli; and performing a certain kind of control by virtue of the identified signal.

P300 is a kind of event related potential (EPR). A peak value will appear in brain electrical signal in 300 ms after the occurring of the related event, which is called as P300. Farwell and Doncin designed a virtual printer by virtue of EPR. A 6*6 character matrix scintillates randomly by row or column, and the scintillating of the row or column containing the character to be entered by the user is the related event. Find out the row and column causing the maximum amplitude of P300, then the character on the intersecting point of the row and the column is the character to be printed.

Sutter's BCI system utilizes visually-evoked potential (VEP) method. A 8*8 symbol matrix on a display appears as red/green alternation in a pseudo-random binary order. The user looks at the character to be chosen, compares the detected brain electrical signal with a prerecorded template, then may confirm the target at which the user is looking. Previously learning to obtain a steady template is a critical step ("The Brain Response Interface: Communication through Visually-evoked Electrical Brain Response", J Microcomput Appl, 1992, 15:31–45).

The above system utilizes instantaneous evoked response. As the basis of the testing is P300, so it is required that the time interval between two stimuli to be more than 1 second, so as to ensure that the response of the subject to the preceding stimulus has ended or disappeared before the arrival of a new stimulus. Thus, the system cannot be used for real-time control, and the reliability of the test cannot fulfill practical requirement too.

Up to date, another primary disadvantage of brain-machine interface method as one of testing technique is the lack of ability to give sense organ stimulus mode with space information simultaneously. Thus, there is no space resolution information of sense organ system in the testing result, so the scope of application is greatly limited.

OBJECT OF THE INVENTION

One object of the invention is to provide a reliable control method and system based on steady state brain evoked response, which may not only achieve very high accuracy of judgment, but also ensure real time processing in use.

Another object of the invention is to provide a sense organ testing method and system based on steady state brain evoked response, which may evaluate objectively the condition of a sense organ.

SUMMARY OF THE INVENTION

The basis of the present invention is steady state brain evoked response. So-called steady state brain evoked response means that when the stimulus frequency is greater than a value, the preceding and forthcoming brain electrical response signals of the subject will overlap, which results in that the brain electrical evoked potential presents a characteristic of periodic change. The frequency of the periodic change consists with the stimulus frequency. As an example of visually evoked repose, if the stimulus frequency is greater than 6 hertz, there will appear periodic change of corresponding frequency in the visually evoked potential of the subject. Utilizing steady state brain evoked response for testing brain activity of a subject, the accuracy and the rate of testing reach the level to perform real time control.

According to one aspect of the invention, there is provided a control method based on steady state brain evoked response comprising the steps of:
  a. generating one or multiple stimulus signals varying in various frequencies that can be sensed by sense organs of human subject;
  b. detecting the brain electrical signal of stimulated human subject;
  c. analyzing the detected brain electrical signal to extract a characteristic physical quantity corresponding to the frequency of one of the stimulus signal as a control signal; and
  d. on the basis of said control signal, controlling a device corresponding to the stimulus signal to perform a preprogrammed operation.

According to another aspect of the invention, there is provided a sense organ testing method based on steady state brain evoked response, the method comprising the steps of:
  a. Stimulating a sense organ of a human subject with one or multiple stimulus signals varying in various frequencies, which can be sensed by sense organs of the human subject;
  b. detecting the brain electrical signal of the stimulated human subject;
  c. analyzing the detected brain electrical signal to extract a characteristic physical quantity corresponding to the frequency of one stimulus signal; and
  d. on the basis of the extracted characteristic physical quantity corresponding to the frequency of the stimulus signal and the intensity and spatial distribution feature etc. of the stimulus signal, evaluating the condition of the tested sense organ.

According to a further aspect of the invention, there is provided a control system based on steady state brain evoked response comprising:
  a. a stimulator for generating one or multiple stimulus signals varying in various frequencies that can be sensed by sense organs of human subject;
  b. a brain electrical signal detector for detecting brain electrical signal of stimulated human subject;
  c. a signal processor for analyzing detected brain electrical signal to extract a characteristic physical quantity corresponding to the frequency of one of the stimulus signal as a control signal; and
  d. a controller for controlling a specified device corresponding to the stimulus signal to perform a preprogrammed operation on the basis of the control signal.

According to a further aspect of the invention, there is provided a sense organ testing system based on steady state brain evoked response comprising:
  a. a stimulator for generating one or multiple stimulus signals varying in various frequencies that can be sensed by sense organs of human subject;
  b. a brain electrical signal detector for detecting brain electrical signal of stimulated human subject;
  c. a signal processor for analyzing the detected brain electrical signal to extract a characteristic physical quantity corresponding to the frequency of one of the stimulus signal; and
  d. an evaluation device for evaluating the response ability to the stimulus signal of the sense organ to be detected on the basis of the extracted characteristic physical quantity corresponding to the frequency of the stimulus signal and the intensity and spatial distribution feature etc. of the stimulus signal, thereby achieving objective evaluation of the sense organ.

In one embodiment, said stimulus signal is a visual stimulus signal, and said sense organ of human subject is a visual organ.

In another embodiment, said stimulus signal is an auditory stimulus signal, and said sense organ of human subject is an auditory organ.

In a further embodiment, said stimulus signal is a tactual stimulus signal, and said sense organ of human subject is a tactile organ.

Preferably, said analysis includes spectrum analyzing to the brain electrical signal, and said characteristic physical quantity is the spectrum component corresponding to each stimulus signal in said brain electrical signal spectrum.

In one embodiment, a stimulus signal is of single frequency.

In another embodiment, a stimulus signal is a combination of signals having different frequencies.

Potential applications of the invention include:
  1. Offering a way to communicate with and to control peripheral environment for the one who is normal in thought but has obstacle in movement. For example, they may operate their wheelchairs, functional electronic stimulus system or computer by virtue of the brain-machine interface.
  2. Offering people a way to additionally operate peripheral device under some special condition, such as for the pilot under great acceleration.
  3. Offering people a definitely new amusement mode, such as playing electronic game by thought, synthesizing music, and so on.
  4. Providing a method for objectively detecting visual or hearing ability without expression of subjective consciousness by speaking or action of limbs etc. The objectiveness and fairness of such method overcome the artificially imposed voluntariness of traditional hearing or visual ability test.
  5. Offering people a visual consciousness condition analysis under special environment, such as the pilot under great acceleration, weary or drunk driver etc.

PREFERRED EMBODIMENTS OF THE INVENTION

Referring now to the accompanying drawings, the current preferred embodiments of the invention will be described in detail.

Figure 1:
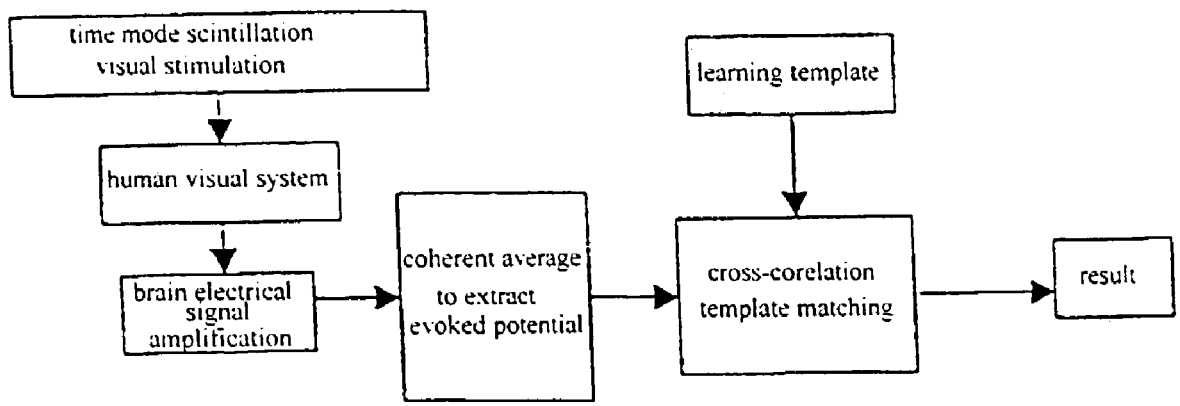
FIG. 1 is a schematic diagram showing the prior art detecting system based on evoked brain electrical signal.
Figure 2:
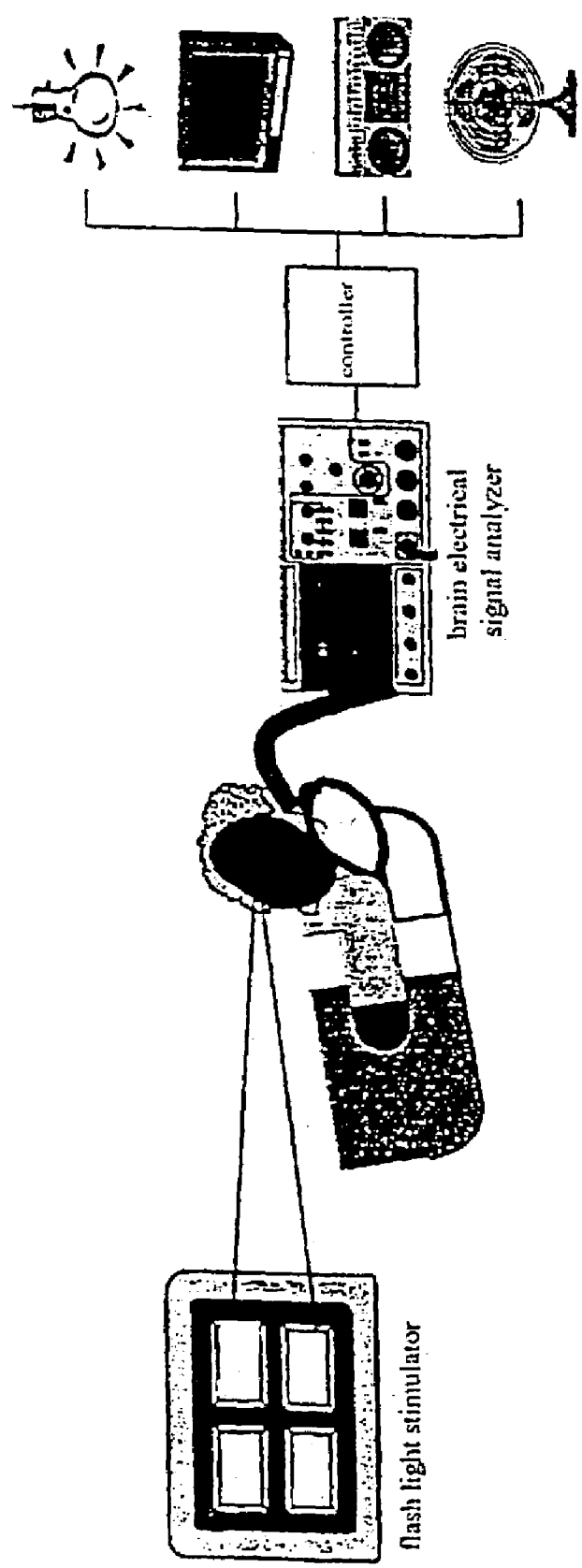
FIG. 2 is a schematic diagram showing the practical structure of the control system based on the steady state brain electrical evoked response of the invention.
Figure 3:
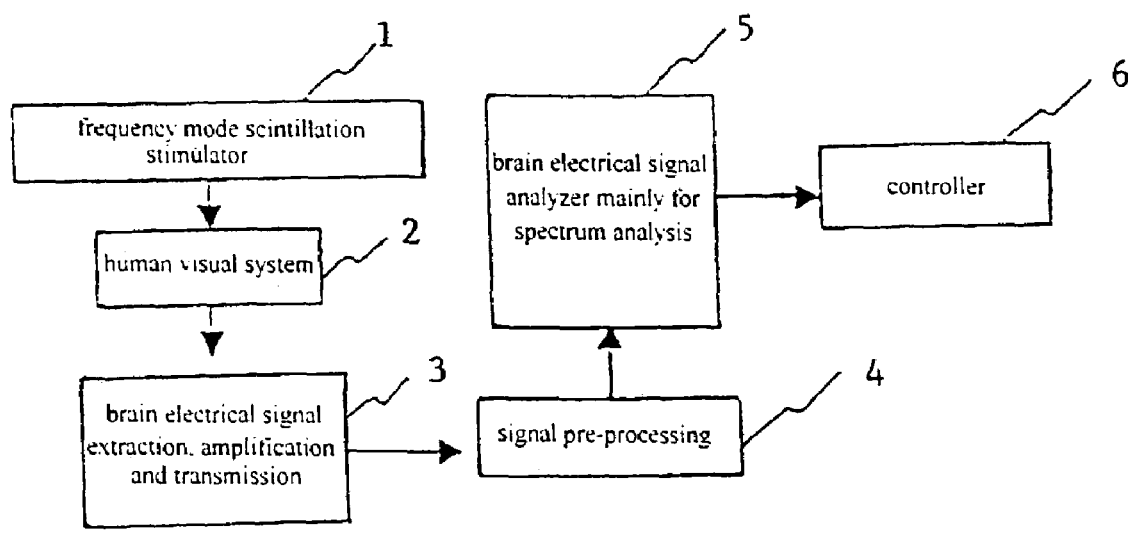
FIG. 3 is a circuit block diagram showing the control system based on the steady state brain electrical evoked response of the invention.

The control system based on the steady state brain electrical evoked response of the invention is shown in FIG. 2 and FIG. 3. The system consists mainly of the following four parts:

1. Stimulator

The function of the stimulator is to produce the stimulus signal to be applied on sense organs of human subject. The stimulus signal can be a visual stimulus signal, a auditory stimulus signal or a tactual stimulus signal. For example of the visual stimulus, the stimulator has some stimulus points which are light sources scintillating in certain frequency. Stimulus points may be flash lamps, other light sources with certain brightness, or the scintillating light spots on a computer screen. Here scintillation means that the brightness, shape, color, size, position, duration or the combination of these physical quantities of the light source varies in certain frequency. The varying frequency of the visual stimulus signal is generally in the range of 1–50 hertz, and preferably in the range of 4–25 hertz.

A stimulus point may be of a signal scintillating in a single frequency, or may contain multiple signals scintillating in various frequencies as well. The advantage of a stimulus point containing multiple signals of various frequency is that, the characteristic response to that stimulus point in the subject's brain electrical signal is the composite spectrum of the multiple frequencies, thereby it is possible to set even more stimulus points in a given frequency range.

The stimulator may have a stimulus controller used to control the characteristic of the stimulus point. As an example of visual stimulus point, the characteristics of the stimulus point include: a) depending on different request of the measurement of the visual system, giving a pre-stimulus prior to the light stimulus; b) setting the background of light stimulus; and c) setting the light stimulus point parameters (spatial position, intensity, area size and duration etc.) of various scintillation frequencies.

2. Brain Electrical Signal Extraction, Amplification and Transmission

The function of brain electrical signal extraction, amplification and transmission is to amplify the weak brain electrical signal to the amplitude enough to be analog-to-digital converted, to perform A/D conversion, and finally, to transmit the converted signal to a computer or other signal processor. The above functions are performed by the following parts:

a. Electrodes: The electrode is a metal chip that is closely stuck on the scalp of the subject, which can detect the variation of the potential on the surface of the scalp (Such variation represents the electrical activity of the brain). The potential variation on the electrodes is the input signal of a brain electrical signal amplifier. The amplitude of the signal is of 1~10 uV.

b. Brain electrical signal amplifier: The function of the brain electrical signal amplifier is to amplify the weak brain electrical signal to an amplitude enough to be analog-to-digital converted. It is generally required that the brain electrical signal amplifier is an electrical physiological signal amplifier with a gain of 3000~10000 and a frequency bandwidth of 1~30 hertz.

c. Signal transmission device: The signal transmission device is used for transmitting the digitized brain electrical signal to a computer or other signal-processing device. Transmission may be carried with wire or wirelessly as well. The transmission delay time should be less than 10 ms.

3. Brain Electrical Signal Processor

Electrical physiological experiments prove that, when giving certain stimulus to the sense organs of a human subject, provided the sense system of the subject is in good health, it is possible to record the evoked brain electrical signal having obvious characteristics from the occipital scalp of the subject. The characteristics of the recorded signal are expressed in time domain, space domain and frequency domain. The function of the brain electrical signal processor is to analyze the characteristics of the brain electrical signal, and identify these characteristics for the purpose of control etc.

As an example of steady state visual stimulus, the main functional modules in the brain electrical signal analyzer include:

a. Brain electrical signal pre-processing: As recorded brain electrical signal is very weak, it will generally be subjected to interference in the extracting process. So Noise-reducing etc. preprocessing is necessary prior to analyzing the signal. Noises that have to be eliminated are mainly power suply interference, baseline drift etc. Noise-reducing processing is usually made by virtue of digital filtering.

b. Brain electrical signal spectrum analyzer: As an example of steady state visual evocation, a stimulus point is a light source scintillating in given frequency, while the brain evoked electrical signal contains the frequency component of the stimulus signal and its harmonic components. In order to obtain these frequency components, the obtained brain evoked electrical signal needs to be spectrum analyzed. This is the function of the spectrum analyzer.

Spectrum analysis is generally fulfilled by a computer or other digital signal processor. Therefore, it is a digital signal processing process. A conventional algorithm used to fulfill spectrum analysis is Fast Fourier Transform (FFT), its formula is $$X(k) = \sum_{n=0}^{N-1} x(n)(e^{-j\frac{2\pi}{N}})^{nk}$$

Here, x (n) represents the digitized brain electrical signal, n=0~N−1; X(k) is the discrete FFT of x (n), k=0~N−1.

c. Frequency characteristic analysis: To fulfill control of different requirement, design stimulus points scintillating in various frequencies or frequency compositions. When the subject looks at a stimulus point according to his desire, there should contain the scintillating frequency and its harmonic components of the stimulus point in the his brain evoked electrical signal. If the stimulus point scintillates in a composition of multi frequencies (for example, its intensity varies in a frequency while its size varies in another frequency), the brain evoked electrical signal of the subject should also contains a nonlinear components (such as sum frequency and difference frequency) of the scintillating frequency composition of the stimulus point. Provided that different frequency components can be resolved by the spectrum analyzer, it is possible to identify a stimulus point or multiple stimulus points being looked at by the subject. To efficiently determine from the frequency spectrum analysis result if the frequency components of a stimulus signal exist, the spectrum peak resolution accuracy and the threshold value for determining spectrum peak are two critical factors in the frequency characteristic analysis. In a preferred scheme, we take the following two measurement. (1) To increase the resolution accuracy of spectrum peak, FFT data should have a certain length, normally 1 second. (2) in FFT result, if a peak value appears in a stimulus frequency, and the ratio of the amplitude of the peak to the maximum value of 4–35 hertz in that FFT result exceeds 0.8, it is determined that the subject is looking at the stimulus point scintillating in that frequency, and if there are more than one stimulus frequencies satisfy this condition, then the frequency with the highest ratio is taken for candidate.

4. Controller

After identified, the brain electrical signal with certain characteristic can be utilized to attain the purpose of certain control operation.

A typical application of the brain-machine interface is provided for handicapped persons to perform the control of some devices, such as turning on/off a light, a TV, an electric fan, etc. According to the output of the brain electrical signal processor, it can be known which scintillating light or point the subject is looking at, thus what control he wants to make is known. If such information is transmitted to an environment controller and corresponding circuit is turned on, the control of periphery device is performed.

In FIG. 2 there is shown a practical example of control system based on steady state brain evoked response of the invention. In the system, the stimulator is a screen, on which four light spots respectively corresponding to four electric apparatuses to be controlled are set. The four light spots scintillate in different frequencies respectively. When the user looks at a light spot corresponding to an apparatus to be controlled, the brain electrical signal processor can detect the frequency peak in his brain electrical signal corresponding to scintillating frequency of the light spot, and output a relevant signal to the controller. The controller controls the corresponding electric apparatus upon that signal to perform preset operation, such as an ON/OFF operation.

FIG. 3 is the circuit block diagram of the system shown in FIG. 2. Reference numeral 1 denotes a frequency mode scintillation stimulator having different stimulus points of various frequencies. Numeral 2 is the visual system of the subject. Numeral 3 denotes the devices for the extraction, amplification and transmission of brain electrical signal, which extracts the brain electrical signal of the subject, amplifies and analog-digital converts the signal, and then transmits the resulting signal to a signal preprocessing device. Numeral 4 denotes the signal preprocessing device for performing a preprocessing of noise-reduction etc. Numeral 5 is a brain electrical signal analyzer for performing mainly the spectrum analysis of the detected brain electrical signal to find out the frequency components corresponding to the frequency of a stimulus point of the scintillation stimulator, thereby determining the scintillating light point followed by the subject and outputting relevant signal to a controller. Numeral 6 is the controller. When receive a signal from the controller, it instructs a corresponding device to perform relevant operation according to a preset program. The principle behind the brain electrical signal analyzer 5 has been illustrated before, so will not be repeated here.

Figure 4:
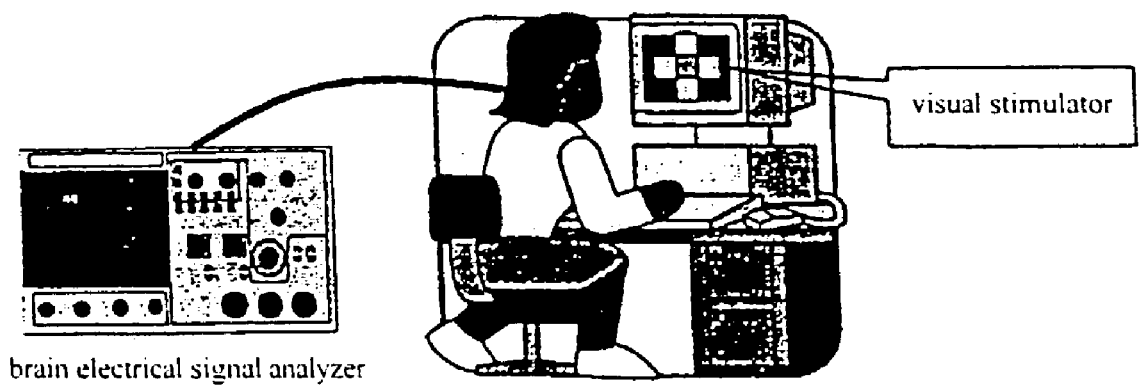
FIG. 4 is a schematic diagram showing the practical structure of the sense organ testing system based on the steady state brain electrical evoked response of the invention.
Figure 5:
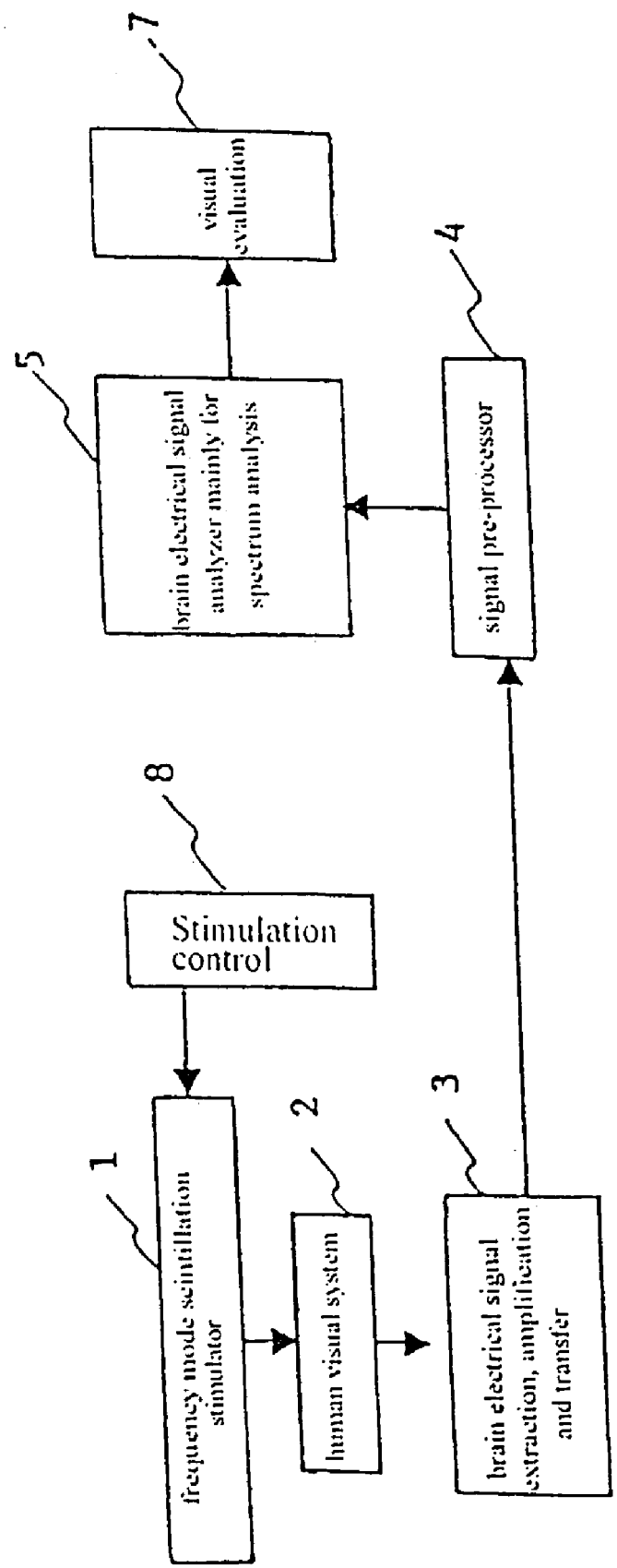
FIG. 5 is a circuit block diagram showing the sense testing system based on the steady state brain electrical evoked response of the invention.

After being identified, the brain electrical signal with given characteristics can be utilized as index to objectively evaluate the sense organ systems of the human subject. FIG. 4 and FIG. 5 show a sense organ testing system based on steady state brain evoked response of the invention. The system is basically identical to the control system shown in FIG. 2 and FIG. 3, but an evaluation device 7 substitutes the control device 6, and a stimulus controller 8 is added.

As an example, a objective visual test comprise the following steps:

(a) In accordance with test requirement of the visual system, giving pre-stimulus prior to light stimulus;

(b) Setting background of light stimulus;

(c) Setting light stimulus point parameters (such as space position, light intensity, light spot size and time duration) of various scintillating frequencies by means of the stimulus controller 8;

(d) Upon the brain evoked electrical signal of the subject, analyzing the response of the subject to various light stimulus points, and attaining an objective evaluation of the subject's visual system in conjunction with the light stimulus point parameters (space position, light intensity, light spot size and time duration etc) and the visual system structure of human subject;

(e) Returning to step (b) if new conditions (such as background and light stimulus point parameters) need to be set, otherwise going to step (f); and (f) Attaining indexes of general objective visual system evaluation of the subject based on objective the visual evaluations under various conditions.

As an example of test embodiment, we carried out a visual system test experiment on a subject based on steady state visually evoked brain potential. The structure of the experiment system is shown in FIG. 4.

Five scintillating block areas is designed on a computer screen with each area scintillating in one or multiple frequency respectively. The block areas are allocated in such a way that one is in the center and other four are around it, respectively positioned on the up side, down side, left side and right side. The subject is required to look at the central block area in progress of the experiment and the frequency components corresponding to the particular frequency characteristic of central area occurs in his brain electrical signal. With the decrease of the sizes of the five scintillating block areas, other frequency components corresponding to the frequency characteristics of other block area will occur in his brain electrical signal. The brain electrical signal analyzer collects and analyzes the brain evoked electrical signal of the subject and the visual ability of the subject could be detected objectively.

The device used for extraction and amplification of the brain electrical signal in the experiment is an existing electroencephalogram machine. Amplified brain electrical signal is input into the brain electrical signal processor constituted of a computer. The computer performs preprocessing and spectrum analyzing of the brain electrical signal to get relevant frequency components. Then the vision level of the subject is determined by means of predetermined computer program.

The experiment is successful. The objective vision detection accurately gives out the visual ability of different subjects.

While as an example the invention has been illustrated in detail in terms of the visual stimulus and response, the invention is not restricted to visual stimulus and response. The stimulator of the invention may be the audio stimulator, tactual stimulator etc. as well, and the steady state brain evoked response of the subject will also include the frequency components corresponding to the frequency of such stimulus signal. On the basis of this feature, it is possible to perform brain electrical control and objective evaluation of the relevant sense organs by means of the analysis of brain evoked response to the audio stimulus, tactual stimulus etc.

Forgoing detailed description in conjunction with accompanying drawings is not intended to limit the scope of the invention. The scope of the invention should only be defined by appended claims. It is not difficult for those skilled in the art to realize other embodiments and applications without departing from the spirit and scope of the invention. Those embodiments and applications should of course belong to the scope of the invention without.

The invention claimed is:

1. A control method based on steady state brain evoked response comprising the steps of:
   a. generating one or multiple stimulus signals varying in various frequencies that can be sensed by sense organs of human subject;
   b. detecting the brain electrical signal of stimulated human subject;
   c. analyzing the detected brain electrical signal to extract a characteristic quantity corresponding to the frequency of one of the one or multiple stimulus signals as a control signal; and
   d. on the basis of said control signal, controlling a device corresponding to the stimulus signal to perform a preprogrammed operation.

2. A control method according to claim 1, wherein said multiple signals varying in various frequencies correspond to multiple different devices to be controlled respectively.

3. A control method according to claim 1 or 2, wherein said one or multiple stimulus signals are visual stimulus signals, and said sense organ of human subject is a visual organ.

4. A control method according to claim 3, wherein at least one of said one or multiple visual stimulus signals is a light signal, the brightness, shape, color, size, position, duration or their combination of which varies in a frequency.

5. A control method according to claim 3, wherein each of said one or multiple visual stimulus signals has a frequency of 1–50 hertz.

6. A control method according to claim 5, wherein each of said one or multiple visual stimulus signals has a frequency of 4–25 hertz.

7. A control method according to claim 3, wherein said multiple visual stimulus signals are a group of spots scintillating in various frequencies on a screen, each spot corresponding to a device to be controlled respectively.

8. A control method according to claim 3, wherein at least one of said one or multiple visual stimulus signals is a combination of multiple light signals which overlap in space and scintillate in various frequencies, and said characteristic quantity is a composition of frequency components corresponding to the composition of the various frequencies of said combination of multi light signals in the detected brain electrical signal.

9. A control method according to claim 1 or 2, wherein said one or multiple stimulus signals are auditory stimulus signals, and said sense organ of human subject is an auditory organ.

10. A control method according to claim 9, wherein at least one of said one or multiple auditory stimulus signals is of a simple tone having a single varying frequency.

11. A control method according to claim 9, wherein at least one of said one or multiple auditory stimulus signal signals is of a composite tone consisting of a specific composition of certain frequencies.

12. A control method according to claim 1 or 2, said one or multiple stimulus signals are tactual stimulus signals, and said sense organ of human subject is a tactile organ.

13. A control method according to claim 1 or 2, wherein said analysis includes spectrum analyzing of the brain electrical signal.

14. A control method according to claim 13, wherein said characteristic physical quantity is a frequency component of a peak of maximum amplitude among the peaks corresponding respectively to said various stimulus signal frequencies in the brain electrical signal spectrum attained from said spectrum analysis.

15. A control method according to claim 13, wherein said characteristic quantity is a frequency component and its harmonic components corresponding to one of said stimulus signal frequencies in the brain electrical signal spectrum attained from said spectrum analysis.

16. A control method according to claim 1 or 2, wherein at least one of said one or multiple stimulus signals is of a single varying frequency.

17. A control method according to claim 1 or 2, wherein at least one of said one or multiple stimulus signals is a combination of multiple signals of different frequencies, and said characteristic quantity is a combination of frequency components corresponding to the combination of frequencies of said combination of multiple signals of different frequencies in the detected brain electrical signal.

18. A sense organ testing method based on steady state brain evoked response, comprising the steps of:
   a. stimulating a sense organ of a human subject with one or multiple stimulus signals varying in various frequencies, which can be sensed by sense organs of the human subject;
   b. detecting the brain electrical signal of the stimulated human subject;
   c. analyzing the detected brain electrical signal to extract a characteristic quantity corresponding to the frequencies of the stimulus signals;
   d. on the basis of the extracted characteristic quantity corresponding to the frequencies of the stimulus signals and the intensity and spatial distribution feature of the stimulus signal, evaluating the condition of the tested sense organ; and
   e. providing an output corresponding to said evaluation.

19. A sense organ testing method according to claim 18, wherein each of said one or multiple stimulus signals is a visual stimulus signal, and said sense organ of human subject is a visual organ.

20. A sense organ testing method according to claim 19, wherein at least one of said one or multiple visual stimulus signals is a light single, the brightness, shape, color, size, position, duration or their combination of which various in frequency.

21. A sense organ testing method according to claim 19 or 20, wherein each of said one or multiple visual stimulus signals has a frequency of 1–50 hertz.

22. A sense organ testing method according to claim 21, wherein each of said one or multiple visual stimulus signals has a frequency of 4–25 hertz.

23. A sense organ testing method according to claim 19 or 20, wherein said one or multiple visual stimulus signals includes a set of light signals being spatially close to each other and scintillating in various frequencies, the spatial characteristics of the spots could be controlled to change.

24. A sense organ testing method according to claim 19, wherein at least one of said one or multiple visual stimulus signals is a combination of multiple light signals which overlap in space and scintillate in various frequencies.

25. A sense organ testing method according to claim 18, wherein each of said one or multiple stimulus signals is an auditory stimulus signal, and said sense organ of human subject is an auditory organ.

26. A sense organ testing method according to claim 25, wherein at least one of said one or multiple auditory stimulus signals is of a simple tone of a single varying frequency.

27. A sense organ testing method according to claim 25, wherein at least one of said one or multiple auditory stimulus signals is of a composite tone consisting of a specific composition of certain frequencies.

28. A sense organ testing method according to claim 18, wherein each of said one or multiple stimulus signals is a tactual stimulus signal, and said sense organ of human subject is a tactile organ.

29. A sense organ testing method according to claim 18, wherein said analysis includes spectrum analyzing of the brain electrical signal.

30. A sense organ testing method according to claim 29, wherein said characteristic quantity is the frequency spectrum components corresponding to the various stimulus signal frequencies in the brain electrical signal spectrum obtained by said spectrum analysis.

31. A sense organ testing method according to claim 29, wherein said characteristic quantity are the frequency components corresponding to said various stimulus signal frequencies the their harmonic components in the brain electrical signal spectrum obtained from said spectrum analysis.

32. A sense organ testing method according to claim 18, wherein at least one of said one or multiple stimulus signals is of a single varying frequency.

33. A sense organ testing method according to claim 18, wherein at least one of said one or multiple stimulus signals is a combination of multiple signals of different frequencies, and said characteristic quantity is a combination of frequency components corresponding to the combination of frequencies of said combination of multiple signals of different frequencies in the detected brain electrical signal.

34. A control system based on the steady state brain evoked response comprising:
   a. a stimulator for generating one or multiple stimulus signals varying in various frequencies that can be sensed by sense organs of human subject;
   b. a brain electrical signal detector for detecting brain electrical signal of a stimulated human subject;
   c. a signal processor for analyzing detected brain electrical signal to extract a characteristic quantity corresponding to the frequency of one of the one or multiple stimulus signals as a control signal; and
   d. a controller for controlling a specified device corresponding to the stimulus signal to perform a preprogrammed operation on the basis of the control signal.

35. A control system according to claim 34, wherein said multiple signals varying in various frequencies correspond to multiple different devices to be controlled respectively.

36. A control system according to claim 34 or 35, wherein each of said one or multiple stimulus signals is a visual stimulus signal, and said sense organ of human subject is a visual organ.

37. A control system according to claim 36, wherein at least one of said visual stimulus signals is a light signal, the brightness, shape, color, size, position, duration or their combination of which various in a frequency.

38. A control system according to claim 36, wherein each of said one or multiple visual stimulus signals has a frequency of 1–50 hertz.

39. A control system according to claim 38, wherein each of said visual stimulus signals has a frequency of 4–25 hertz.

40. A control system according to claim 36, wherein said one or multiple visual stimulus signals are a group of spots scintillating in various frequencies on a screen, each spot corresponds to a device to be controlled respectively.

41. A control system according to claim 36, wherein at least one of said one or multiple visual signals is a combination of multi light signals overlapping in space and scintillating in different frequencies.

42. A control system according to claim 34 or 35, wherein each of said one or multiple stimulus signals is an auditory stimulus signal, and said sense organ of human subject is an auditory organ.

43. A control system according to claim 42, wherein at least one of said one or multiple auditory stimulus signals is of a simple tone having a single varying frequency.

44. A control system according to claim 42, wherein at least one of said one or multiple auditory stimulus signals is of a composite tone consisting of a specific composition of certain frequencies.

45. A control system according to claim 34 or 35, wherein each of said one or multiple stimulus signals is a tactual signal, and said sense organ of human subject is a tactile organ.

46. A control system according to claim 34 or 35, wherein said analysis performed by said signal processor includes spectrum analyzing of the brain electrical signal.

47. A control system according to claim 46, wherein said characteristic quantity is a frequency component of a peak of maximum amplitude among the peaks corresponding respectively to said various stimulus signal frequencies in the brain electrical signal spectrum obtained from said spectrum analysis.

48. A control system according to claim 46, wherein said characteristic quantity is a frequency component and its harmonic components corresponding to one of said stimulus signal frequencies in the brain electrical signal spectrum attained from said spectrum analysis.

49. A control system according to claim 34 or 35, wherein at least one of said one or multiple stimulus signals is of a single varying frequency.

50. A control system according to claim 34 or 35, wherein at least one of said one or multiple stimulus signals is a combination of multiple signals of different frequencies, and said characteristic quantity is a combination of frequency components corresponding to the combination of frequencies of said combination of multiple signals of different frequencies in the detected brain electrical signal.

51. A sense organ testing system based on steady state brain evoked response comprising:
   a. a stimulator for generating one or multiple stimulus signals varying in various frequencies that can be sensed by sense organs of a subject;
   b. a brain electrical signal detector for detecting brain electrical signal of stimulated subject;
   c. a signal processor for analyzing the detected brain electrical signal to extract a characteristic physical quantity corresponding to the frequencies of the stimulus signal(s); and
   d. an evaluation device for evaluating the response ability to the stimulus signal(s) of the sense organ to be detected on the basis of the extracted characteristic quantity corresponding to the frequencies of the stimulus signal(s) and the intensity and spatial distribution feature etc. of the stimulus signal, thereby achieving objective evaluation of the sense organ.

52. A sense organ testing system according to claim 51, wherein each of said one or multiple stimulus signals is a visual stimulus signal, and said sense organ of human subject is a visual organ.

53. A sense organ testing system according to claim 52, wherein at least one of said one or multiple visual stimulus signals is a light signal, the brightness, shape, color, size, position, duration or their combination of which varies in a frequency.

54. A sense organ testing system according to claim 52 or 53, wherein each of said one or multiple visual stimulus signal has a frequency of 1–50 hertz.

55. A sense organ testing system according to claim 54, wherein each of said one or multiple visual stimulus signal has a frequency of 4–25 hertz.

56. A sense organ testing system according to claim 52 or 53, wherein said one or multiple visual stimulus signals are a group of spots scintillating in various frequencies on a screen, each spot corresponds to a device to be controlled respectively.

57. A sense organ testing system according to claim 52 or 53, wherein at least one of said one or more visual signals is a combination of multi light signal overlapping in space and scintillating in different frequencies.

58. A sense organ testing system according to claim 51, wherein each of said one or multiple stimulus signals is an auditory stimulus signal, and said sense organ of human subject is an auditory organ.

59. A sense organ testing system according to claim 58, wherein at least one of said one or multiple auditory stimulus signals is of a simple tone having a single varying frequency.

60. A sense organ system according to claim 58, wherein at least one of said one or multiple auditory stimulus signals is of a composite tone consisting of a specific composition of certain frequencies.

61. A sense organ testing system according to claim 51, wherein each of said one or multiple stimulus signals is a tactual stimulus signal, and said sense organ of human subject is a tactile organ.

62. A sense organ testing system according to claim 51, wherein said analysis performed by said signal processor includes spectrum analyzing of the brain electrical signal.

63. A sense organ testing system according to claim 62, wherein said characteristic quantity is the frequency components corresponding to said various stimulus signal frequencies in the brain electrical signal spectrum obtained from said spectrum analysis.

64. A sense organ testing system according to claim 51, wherein at least one of said one or multiple stimulus signals is of a single varying frequency.

65. A sense organ testing system according to claim 51, wherein at least one of said one or multiple stimulus signals is a combination of multiple signals of different frequencies, and said characteristic quantity is a combination of frequency components corresponding to the combination of frequencies of said combination of multiple signals of different frequencies in the detected brain electrical signal.

* * * * *